(12) United States Patent
Bruckner et al.

(10) Patent No.: US 6,221,005 B1
(45) Date of Patent: Apr. 24, 2001

(54) PUBO-URETHRAL SUPPORT HARNESS APPARATUS FOR PERCUTANEOUS TREATMENT OF FEMALE STRESS URINARY INCONTINENCE WITH URETHAL HYPEMOBILITY

(76) Inventors: Norman I. Bruckner, 3432 Brookshire Dr., Plano, TX (US) 75075; Guillermo H. Davila, 2580 SE. 8th St., Pompano Beach, FL (US) 33062

(*) Notice: Subject to any disclaimer, the term of this patent is extended or adjusted under 35 U.S.C. 154(b) by 0 days.

(21) Appl. No.: 09/390,901

(22) Filed: Sep. 7, 1999

Related U.S. Application Data

(63) Continuation-in-part of application No. 09/024,701, filed on Feb. 17, 1998, now Pat. No. 6,068,591.

(51) Int. Cl.[7] ............................................. A61F 2/02
(52) U.S. Cl. ................................. 600/30; 128/DIG. 25
(58) Field of Search ............................. 600/29–31, 37; 606/151; 128/897–98, DIG. 25

(56) References Cited

U.S. PATENT DOCUMENTS

| | | | |
|---|---|---|---|
| 6,042,534 | * | 3/2000 | Gellman et al. ................... 600/30 |
| 6,042,536 | * | 3/2000 | Tihon et al. ...................... 600/30 |
| 6,117,067 | * | 9/2000 | Gil-Vernet ....................... 600/30 |

* cited by examiner

*Primary Examiner*—John P. Lacyk
(74) *Attorney, Agent, or Firm*—Norman I. Bruckner; Guillermo H. Davila

(57) ABSTRACT

An apparatus for treatment of female stress urinary incontinence with urethral hypermobility with a support harness adapted to fit over the superior edge of the pubic bone of a patient, left or right of the pubis symphysis, a sling adapted to rest against the anterior vaginal wall or submucosally at the level just below the urethrovesical junction, and vaginal shaft connecting the sling to the support harness and adapted to position the sling causing stabilization and support of the urethrovesical junction.

19 Claims, 4 Drawing Sheets

PUBO-URETHRAL SUPPORT HARNESS APPARATUS FOR PERCUTANEOUS TREATMENT OF FEMALE STRESS URINARY INCONTINENCE WITH URETHAL HYPEMOBILITY

CROSS-REFERENCE TO RELATED APPLICATION

This is a continuation-in-part of application Ser. No. 09/024,701 filed Feb. 17, 1998, now U.S. Pat. No. 6,068,591 titled, "Apparatus for Female Urinary Incontinence."

BACKGROUND OF THE INVENTION

This invention relates to medical devices as alternatives for surgical correction of anatomic female stress urinary incontinence with urethral hypermobility (referred to as SUI) and more particularly to a Pubo-Urethral Support Harness Apparatus (referred to as a "PUSH apparatus") for Percutaneous Treatment of Female Stress Urinary Incontinence with Urethral Hypermobility.

The present invention relates to SUI and provides an apparatus and method for treatment. More specifically, this invention relates to an apparatus and method of stabilizing and supporting the urethrovesical junction without use of sutures, staples or bone anchors to correct female stress urinary incontinence with urethral hypermobility.

Anatomic SUI with urethral hypermobility is a condition that is accompanied by the involuntary loss of urine during coughing, laughing, sneezing or other exertional physical activities. SUI is most often caused by weakening of the supporting endopelvic fascia and muscles resulting in the abnormal movement of the urethra and bladder neck with increased intra-abdominal pressure. Continence is re-established by stabilizing and supporting the urethrovesical junction thereby allowing the bladder neck remain in its physiologic position.

SUI interferes with a woman's ability to lead a normal life. SUI impacts a woman's self-esteem, often leads to embarrassment and limits her capacity to fulfill her social and family roles. Women address this condition by: managing the problem with absorbent products; undergoing non-surgical treatments such as behavior training, drugs, and using vaginal anatomical support devices; or undergoing surgical intervention. Disadvantages associated with managing the symptoms of SUI include odor and alteration of dress to conceal the presence of a pad or brief. Among the disadvantages associated with non-surgical therapies are poor response to treatment, inconvenience, the need for the patient to be highly motivated, and vaginal discomfort caused by the presence of a support device.

Many surgical procedures involving elevation, stabilization and support to the urethrovesical junction have been devised over the years cure SUI. Robertson, U.S. Pat. No. 5,019,032 describes a method of treatment involving the installation of sutures between the rectus fascia and the vagina using a needle inserted through the abdomen. A urethropexy procedure is disclosed in U.S. Pat. No. 5,013,292 to Lemay and describes burying a pair of implants, one on each side of the pubis symphysis, and threading suture from the vagina through the implants to support the bladder neck. Alternatively, the ends of the sutures can be tied to a saddle member to support the bladder neck. Richardson, U.S. Pat. No. 5,149,329 described stabilization and support to the urethrovesical junction by bringing the paravaginal fascia into juxtaposition with Cooper's ligament through suture placement using a suturing needle assembly. Petros, U.S. Pat. No. 5,112,344 describes looping a filamentary element between the vaginal wall and the rectus abdominis in the anterior wall of the abdomen to provide urethrovesical support. Several common needle suspension procedures for treating SUI have been disclosed over the years including: Pereyra (e.g., West J. Surg. Obst. & Gynec., ppg. 223–226, 1959) in which suture interconnects subcutaneous tissue above the rectus fascia to tissue on both sides of the urethra; Raz (e.g. Urol., Vol. 17 ppg., 82–85,1981) in which suture interconnects subcutaneous tissue above the rectus fascia to the vaginal wall on both sides of the urethra; and Stamey (e.g., Surg. Gyn. & Obst., Vol. 136, ppg. 547–554, April 1973) in which Dacron sleeves, located in tissue on both sides of the urethra are attached to subcutaneous tissue above the rectus fascia. Problems associated with many of these procedures result in suture pull through from the abdominal wall rectus fascia causing reoccurrence of incontinence. In addition, these procedures generally require general anesthesia, lengthy hospitalization and restricted activities for 8 to 12 weeks.

An apparatus for treating SUI by applying an anchoring device to body tissue and adjusting the suture length between anchors using a cinching member is described in U.S. Pat. No. 5,562,689 to Green et al. Blake, U.S. Pat. No. 5,647,836 discloses the use of anchor pairs, each pair interconnected by suture to treat SUI. Endopelvic fascia attached to each side of the urethra is elevated and held in place by a pair of anchors comprised of upper and lower stays, whereby the upper stay is positioned above the rectus fascia. Benderev, U.S. Pat. No. 5,611,515 describes a bladder neck suspension procedure using anchor fixation of the suspending sutures to the pubic bone, and the tools required to perform the procedure. Kovac and Cruikshank, Contemporary OB/GYN, February 1998, describe placement of bone anchors into the inferior border of the pubis to support suspending sutures. The concerns with this technique include development of osteomyelitis and vaginal wall pull through leading to surgical failure.

Although surgery provides the highest success rates among all treatments for SUI, it is not without its problems. Reported drawbacks to surgical therapy include: expenses due to the associated medical and hospitalization costs; possible medical complications such as bleeding and alteration of normal voiding; impact on short-term normal life style activities; and in some instances, require women to modify their life style permanently to retain their continence. Surgery may also require repeat surgery in order to maintain continence.

SUMMARY OF THE INVENTION

The primary object of the invention is to provide effective, long-lasting, therapy for Stress Urinary Incontinence with urethral hypermobility (referred to as SUI) that has minimal impact on life style activities.

Another object of the invention is to provide a treatment SUI that is not prone to medical complications.

Another object of the invention is to provide a treatment for SUI that does not require bone anchors, sutures, staples, or peri-urethral injections for restoration of bladder neck anatomic support.

Yet another object of the invention is to provide a treatment for SUI that is simple, easily-learned, minimally invasive and can be performed as an outpatient procedure under local anesthesia or mild sedation with no post-treatment catheterization.

A further object of the invention is to provide a treatment for SUI that is, if necessary, amenable to adjustment without repeat major surgery.

Another object of the invention is to provide a treatment for SUI that can be performed on women with previous unsuccessful anti-incontinence surgery.

Still yet another object of the invention is to provide a treatment for SUI that can be performed along with other pelvic reconstructive procedures.

Other objects and advantages of the present invention will become apparent from the following descriptions, taken in connection with the accompanying drawings, wherein, by way of illustration and example, an embodiment of the present invention is disclosed.

The present invention comprises an apparatus and a minimally invasive method for treating SUI by stabilizing and supporting the urethrovesical junction. The treatment can be performed in an office or as an outpatient procedure with local anesthesia or mild sedation without use of sutures, staples, bone anchors or peri-urethral injectable bulking agents. The apparatus described in this invention possesses fixably adjustable design features that compensate for anatomic changes that could occur post-operatively causing incontinence or retention to occur.

In accordance with an embodiment of the present invention, an apparatus for treatment of SUI comprises: two support harnesses, each adapted to fit over the superior edge of the pubic bone of a patient, left and right of the pubis symphysis, a sling or hammock adapted to rest against the anterior vaginal wall or positioned submucosally at a level just below the urethrovesical junction, and two shafts, each connecting the sling to a support harness and adapted to maintain the position of the sling thereby stabilizing and supporting the urethrovesical junction. In other embodiments, the support harness and shaft may be of a unitary piece design, the shafts and sling may be of a unitary piece design, or the support harnesses, shaft and sling may be of a unitary piece design. The harness component of the apparatus may be constructed of a material that is shapeable and possesses features for fitting securely over and against the pubic bone. The shaft component may be constructed of shapeable material including wire or synthetic thread. The sling component may be constructed of synthetic or fascia material.

In another embodiment, a method for the treatment of SUI comprises the steps of: (a) Placing patient in the lithotomy position, (b) Penetrating the anterior vaginal wall at a location approximately 2 cm lateral to the urethrovesical junction with the sharp leading end of a directional cannula delivery unit containing a support harness-vaginal shaft assembly, (c) Directing the cannula delivery unit in a cephalad direction along the posterior aspect of the pubic bone over the superior edge of the pubic bone; (d) Advancing the harness end of the support harness-vaginal shaft assembly through the cannula delivery unit, down the anterior aspect of the pubic bone until the tip comes to rest at a position approximately halfway down the anterior aspect of the pubic bone, (e) Withdrawing the cannula delivery unit from the vagina exposing the tail of the vaginal shaft, (f) Coupling one end of the sling onto the vaginal shaft, (g) Adjusting the position of the sling against the anterior vaginal wall, (h) Securing the position of the sling and trimming excess vaginal shaft from the assembly unit, and (i) Repeat steps b-h on the opposite side of the urethrovesical junction using a second support harness-vaginal shaft assembly and the same sling.

In another embodiment, a method for the treatment of SUI comprises the steps of: (a) Placing patient in the lithotomy position, (b) Penetrating the abdominal wall at a location above the pubic symphysis and left of midline with the sharp leading end of a directional cannula delivery unit containing a support harness-vaginal shaft assembly, (c) Directing the cannula delivery unit in a downward direction along the posterior aspect of the pubic bone penetrating the anterior vaginal wall and coming to rest just below the superior edge of the pubic bone; (d) Directing the cannula delivery unit over the superior edge of the pubic bone; (e) Advancing the shaft end of the support harness-vaginal shaft assembly through the cannula delivery until the tip comes to rest in the vaginal cavity at a position approximately 2 cm lateral to the urethrovesical junction, (f) Advancing the harness end of the support harness-vaginal shaft assembly up through the cannula delivery unit, down the anterior aspect of the pubic bone until the tip comes to rest halfway down the anterior aspect of the pubic bone, (g) Withdrawing the cannula delivery unit from the vagina exposing the tail of the vaginal shaft, (h) Coupling one end of the sling onto the vaginal shaft, (i) Adjusting the position of the sling against the anterior vaginal wall, (j) Securing the position of the sling and trimming excess vaginal shaft from the support harness-vaginal shaft assembly, and (k) Repeat steps b–j on the opposite side of the urethrovesical junction using a second support harness-vaginal shaft assembly and the same sling. Close the abdominal wall cannula made incisions.

In all embodiments the sling can be positioned submucosally by making a vertical suburethral incision along the vaginal mucosa of the anterior vaginal wall and dissecting submucosal connective tissue laterally, off of the vaginal wall.

The drawings constitute a part of this specification and include exemplary embodiments to the invention, which may be embodied in various forms. It is to be understood that in some instances various aspects of the invention may be shown exaggerated or enlarged to facilitate an understanding of the invention.

DETAILED DESCRIPTION OF THE PREFERRED EMBODIMENTS

Detailed descriptions of the preferred embodiment are provided herein. It is to be understood, however, that the present invention may be embodied in various forms. Therefore, specific details disclosed herein are not to be interpreted as limiting, but rather as a basis for the claims and as a representative basis for teaching one skilled in the art to employ the present invention in virtually any appropriately detailed system, structure or manner.

A pubo-urethral support harness is described in U.S. Ser. No. 09/024,701, herein incorporated by reference.

Figure 1A:
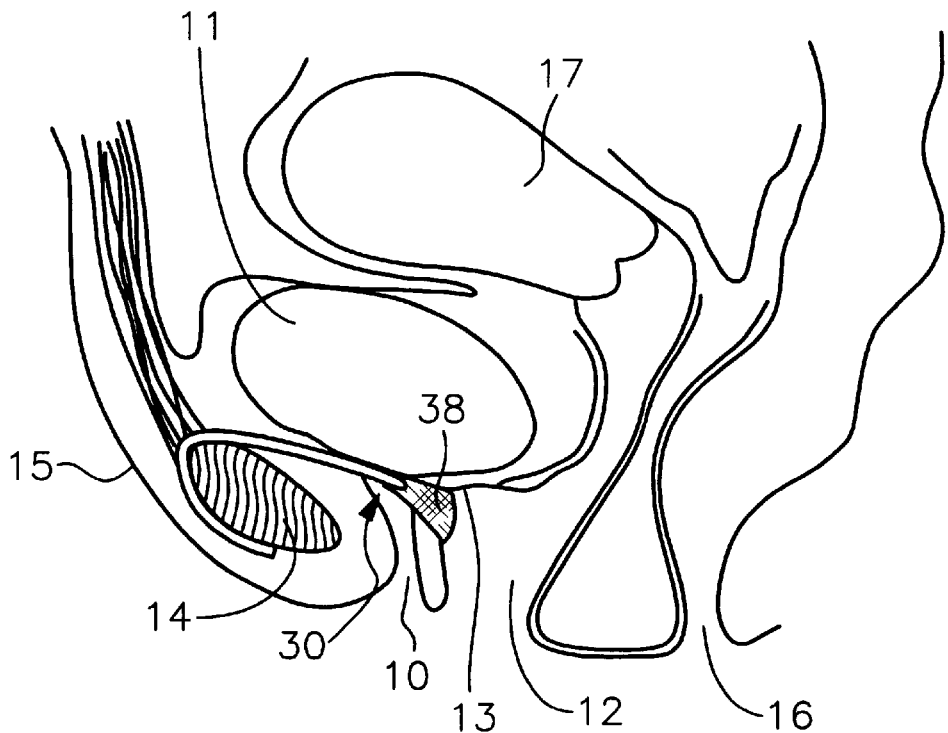
FIGS. 1, a and b, are lateral views of female pelvic anatomy with PUSH apparatus in place in accordance with the present invention.
Figure 1B:
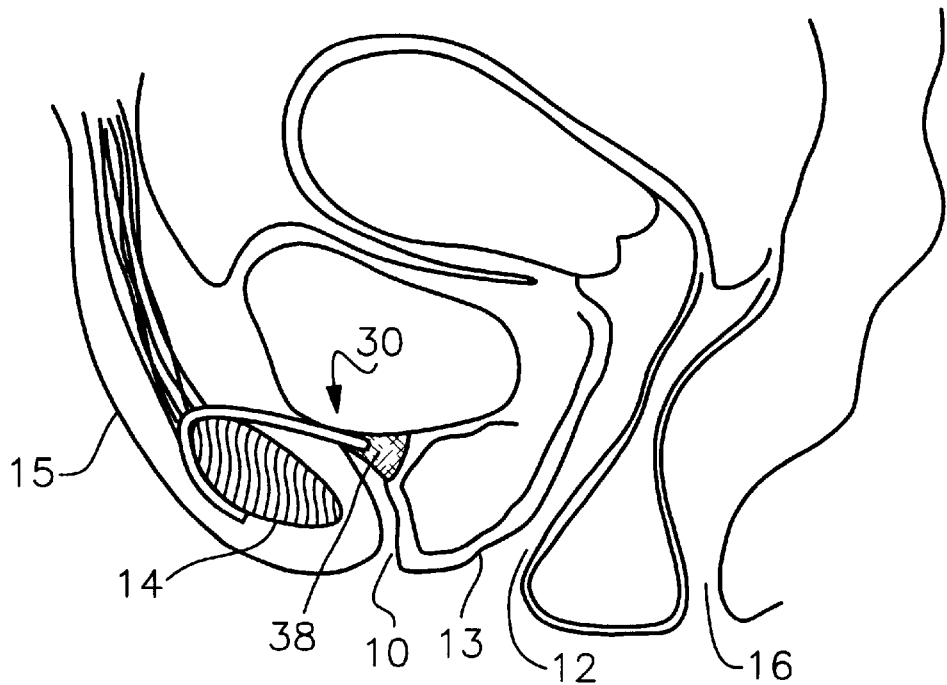
Figure 2:
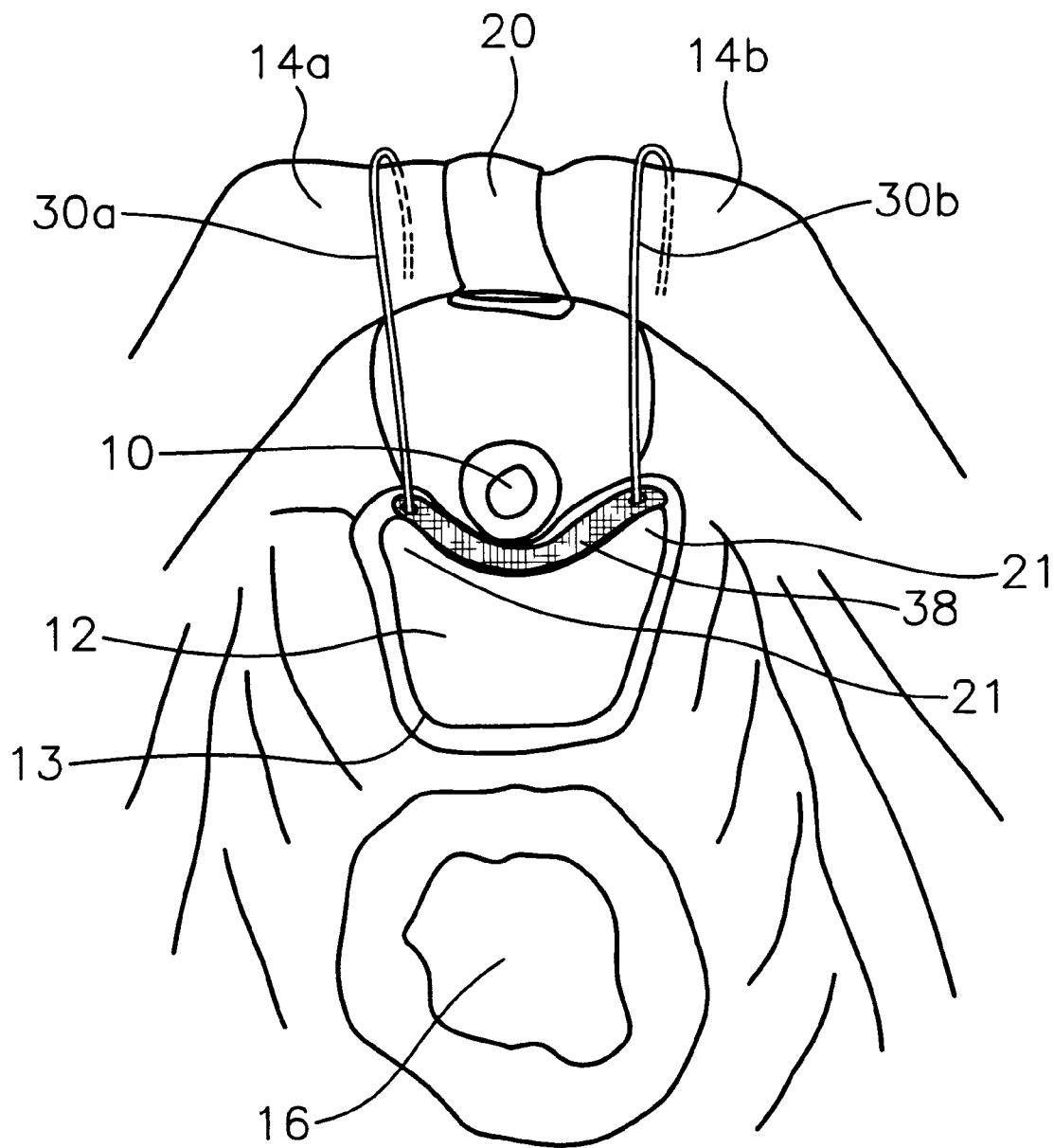
FIG. 2 is a cross-sectional view of urethra with the PUSH apparatus in place in accordance with the present invention.
Figure 3:
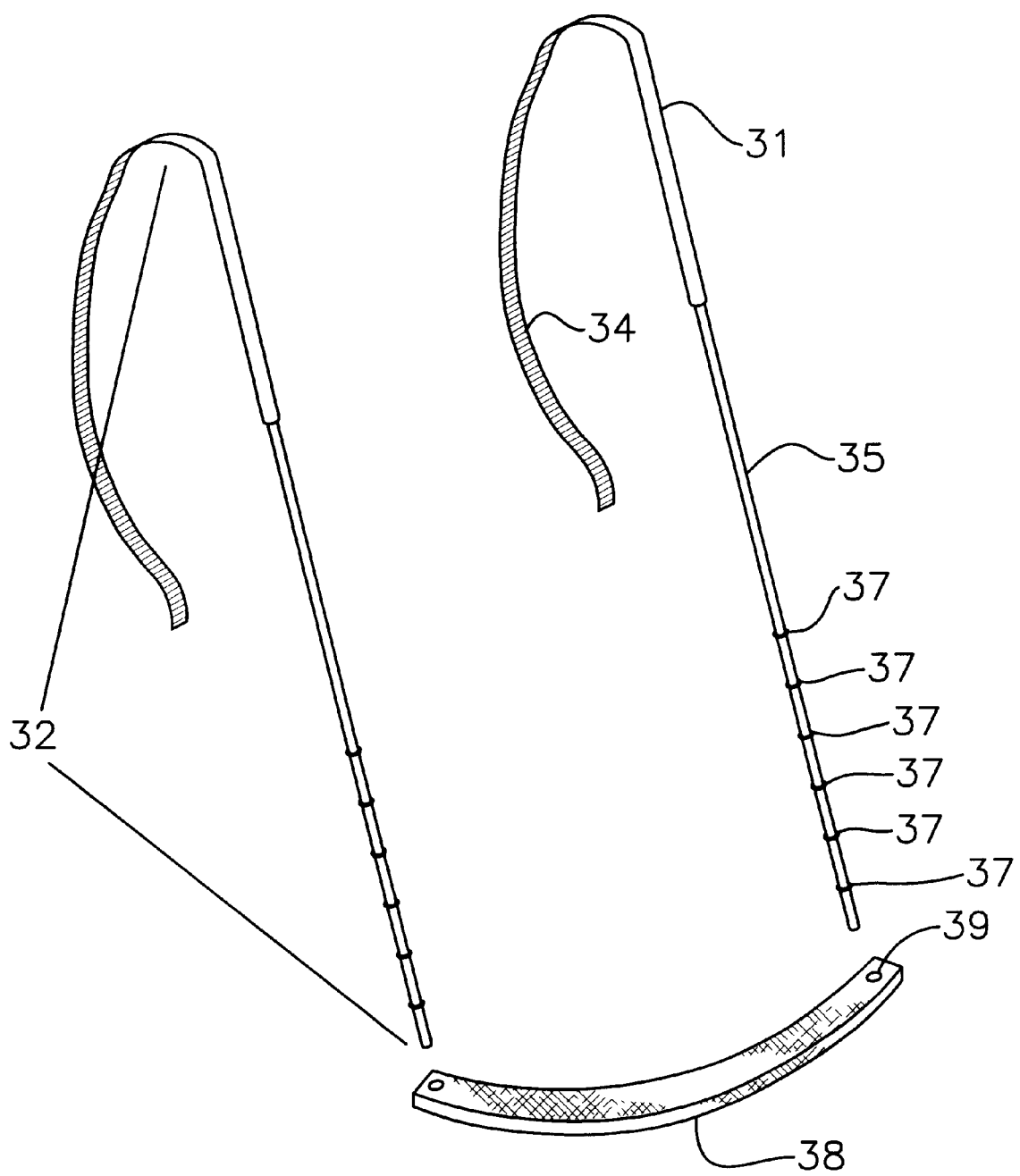
FIG. 3 is a perspective view of the support harness-vaginal shaft assembly with the sling in a fixably adjustable relation according to an embodiment of the present invention.

Turning first to FIGS. 1, a and b, there is shown lateral views of the female pelvic anatomy identified by parts including urethra 10, bladder 11, vagina 12, vaginal wall 13, pubic bone 14, abdominal skin 15, rectum 16 and uterus 17, and the pubo-urethral support harness (referred to as a "PUSH apparatus") 30 positioned to stabilize and support the urethrovesical junction. As shown in FIGS. 1a, 1b and 3, that portion of the PUSH apparatus 30 that fits over the pubic bone is referred to as the "support harness" 31; the part of the apparatus resting up against the anterior vaginal wall (FIG. 1a) or behind the mucosa of the anterior vaginal wall (FIG. 1b) is referred to as the "sling" 38, and the segment of the PUSH apparatus connecting the support harness to the sling is referred to as the "vaginal shaft" 35. FIG. 2 shows a cross sectional view of the proximal urethra identified by parts including urethra 10, vagina 12, vaginal wall 13, rectum 16, vaginal dimples 21, and PUSH apparatus 30a and 30b, each positioned over the pubic bone, left 14a and right 14b of the pubis symphysis 20, both functioning to stabilize and support the urethrovesical junction. The degree of stabilization and support is dependent on the position of the sling relative to the pubic bone and is optimized by the fixably adjustable relation between PUSH apparatus components whereby the relative positioning may be adjustable but fixed once adjusted to the desired positional relationship and may be re-adjusted and fixed in the re-adjusted relation.

In accordance with the present invention, FIG. 3 shows a preferred embodiment of the invention comprising of a single unit support harness-vaginal shaft assembly 32 and separate sling 38. The assembly 32 possesses a support harness serrated surface 34 and fixably adjustable settings 37 on the vaginal shaft 35. Sling 38 possesses fixably adjustable sites 39 that are compatible with the settings 37 on the vaginal shaft. In operation and insertion, the assembled 32 may be loaded into a cannula not shown but known to those in the art. The anterior vaginal wall located approximately 2 cm. lateral to the urethrovesical junction is penetrated with the sharp closed leading end of the loaded cannula. The cannula is directed in a cephalad direction with the leading end adjacent to the posterior aspect of the pubic bone 14 over the superior edge of the pubic bone. The harness end of the assembly is advanced through the cannula delivery unit, down the anterior aspect of the pubic bone until the tip comes to rest at a position approximately halfway down the anterior aspect of the pubic bone. The cannula delivery unit is withdrawn from the vagina exposing the tail of the vaginal shaft. The sling is attached to the vaginal shaft portion of assembly and elevated until the appropriate position on the anterior vaginal wall is achieved. Adjustment of sling position is made using the fixably adjustable relation between assembly and the sling. In this embodiment of the invention, the support harness-vaginal shaft is envisioned as being constructed from a shapeable, superelastic or thermomemory material. Placement of the support harness-vaginal shaft unit is accomplished using a directionally controlled cannula delivery unit. Following the same procedure, a second assembly is positioned on the opposite side of the urethra to produce the desired effect pictured in FIG. 2. Final adjustments are made to achieve the desired stability and support of the urethrovesical junction using the fixably adjustable relationship between the support harness-vaginal shafts and the sites on the sling.

Figure 4A:
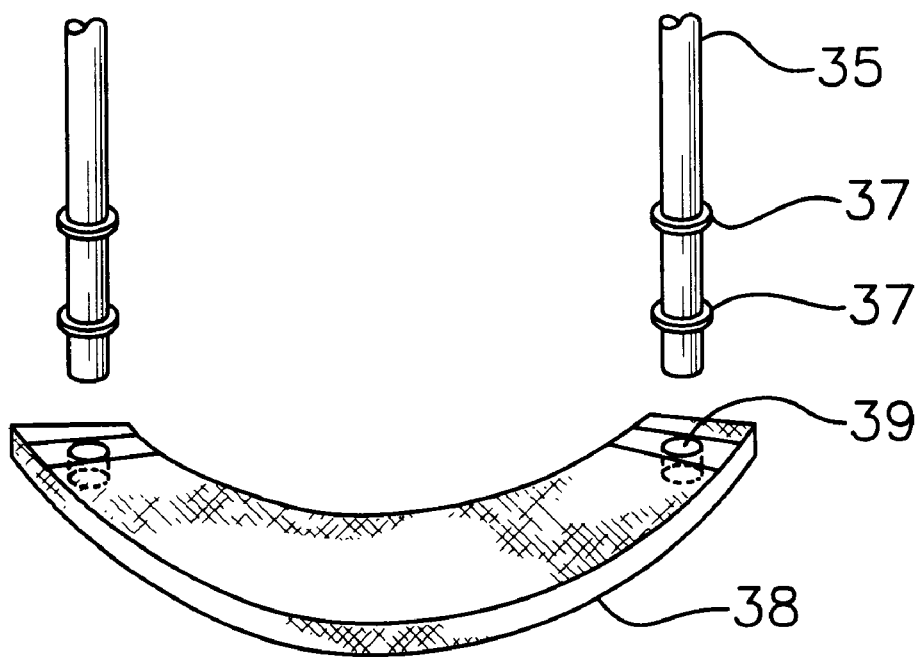
FIG. 4 is a perspective view of the vaginal shaft portion of the support harness-vaginal shaft assembly and sling in fixably adjustable relation according to an embodiment of the present invention.
Figure 4B:
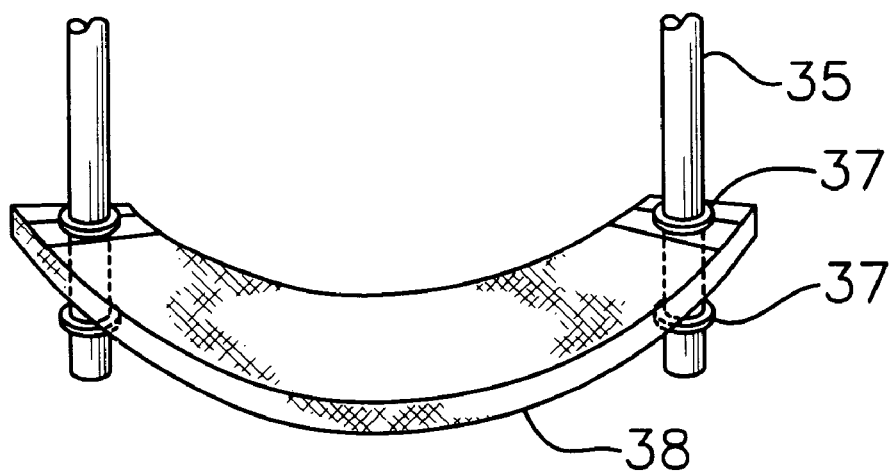

FIG. 4 shows an enlarged view of the fixably adjustable relation between sling 38 and vaginal shaft 35 presented in FIG. 3. Once the appropriate position of the sling on the anterior vaginal wall has been achieved, the sling is secured on the vaginal shaft by placing one of the fixably adjustable settings 37 on shaft 35 through the fixably adjustable site 39 on the sling receiver. Excess shaft is cut at a position posterior to the sling. Alternatives to securing mechanism 37–39 include, but not restricted to, devices such as Carter pins, alignment pins or clips.

In the preferred embodiment shown, the support harness 31 and vaginal shaft 35 are made of materials that are biologically compatible such as those well known in the art [stainless steel, titanium or polypropylene plastic] or coated with a biologically compatible material [polyurethane or silicone]. The sling is made of bio-compatible synthetic material such as those well known in the art [polypropylene, silicone, or polytetrafluoroethylene] or fascia. Further, whether a unitary or multi-piece design, the PUSH apparatus may be made of a shapeable, superelastic or thermomemory material [titanium-nickel alloy]. In all described embodiments, the preferred design of the support harness includes a means for traction against the pubic bone, allowance for the support harness to be hooked onto the pubic bone, or adapted to clamp onto the pubic bone. In all embodiments illustrated, the sling is of a particular size and shape to avoid vaginal wall tear and altering distance between support harness-vaginal shaft assemble units, yet be able to be securely fastened and stayed.

While the invention has been described in connection with several embodiments, it is not intended to limit the scope of the invention to the particular form set forth, but on the contrary, it is intended to cover such alternatives, modifications, and equivalents as may be included within the spirit and scope of the invention as defined by the appended claims.

What is claimed is:

1. An apparatus for treatment of female stress urinary incontinence with urethral hypermobility (referred to as SUI) comprising:

support harnesses adapted to fit over the superior edge of the pubic bone of a patient, left and right of the pubis symphysis;

a sling adapted to rest against the anterior vaginal wall of a patient or submucosally at the level just below the urethrovesical junction;

shafts each integral with a support harness connecting the sling to the support harnesses and adapted to hold the position of the sling causing stabilization and support to the urethrovesical junction; and coupling interfaces between the shafts and sling.

2. An apparatus for treatment of SUI as claimed in 1 wherein the shaft and the sling are in fixably adjustable relation.

3. An apparatus for treatment of SUI as claimed in 1 wherein the support harness and the shaft are in fixably adjustable relation.

4. An apparatus for treatment of SUI as claimed in 1 wherein the support harness, shaft and sling are constructed of material that is biologically compatible.

5. An apparatus for treatment of SUI as claimed in 1 wherein the support harness is constructed of material that is shapeable.

6. An apparatus for treatment of SUI as claimed in 1 wherein the support harness has an anterior end and the anterior end has an interior surface, the interior surface of the anterior end of the support harness is adapted to produce traction against the pubic bone.

7. An apparatus for treatment of SUI as claimed in 1 wherein the shaft is constructed of wire or synthetic thread.

8. An apparatus for treatment of SUI as claimed in 1 wherein the support harness is constructed of superelastic or thermomemory material.

9. An apparatus for treatment of SUI as claimed in 1 wherein the support harness is adapted to hook onto the pubic bone.

10. An apparatus for treatment of SUI as claimed in 1 wherein the support harness is adapted to clamp onto the pubic bone.

11. An apparatus for treatment of female stress urinary incontinence comprising of a single component adapted to form a support harness that fits over the superior edge of the pubic bone of a patient; a sling adapted to engage, stabilize, and support the urethrovesical junction; and shaft connecting the support harness and sling.

12. An apparatus for treatment of SUI as claimed in 11 wherein the apparatus is constructed of material that is biologically compatible.

13. An apparatus for treatment of SUI as claimed in 11 wherein the apparatus is constructed of material that is shapeable.

14. An apparatus for treatment of SUI as claimed in 11 wherein the support harness has an anterior end and the anterior end has an interior surface, the interior surface of the anterior end of the support harness to be is adapted to produce traction against the pubic bone.

15. An apparatus for treatment of SUI as claimed in 11. wherein the apparatus is constructed of superelastic or thermomemory material.

16. A method for the treatment of SUI comprising the steps of, but not necessarily in the order of:
    (a) Placing patient in the lithotomy position;
    (b) Penetrating the anterior vaginal wall at a location approximately 2 cm lateral to the urethrovesical junction with the sharp leading end of a directional cannula delivery unit containing a support harness-vaginal shaft assembly;
    (c) Directing the cannula delivery unit in a cephalad direction along the posterior aspect of the pubic bone over the superior edge of the pubic bone;
    (d) Advancing the harness end of the assembly through the cannula delivery unit, down the anterior aspect of the pubic bone until the tip comes to rest at a position approximately halfway down the anterior aspect of the pubic bone;
    (e) Withdrawing the cannula delivery unit from the vagina exposing the tail of the vaginal shaft;
    (f) Coupling one end of the sling onto the vaginal shaft end of the assembly;
    (g) Adjusting the position of the sling against the anterior vaginal wall until the appropriate position is achieved;
    (h) Securing the position of the sling and trimming excess vaginal shaft from the assembly;
    (i) Repeat steps b–h on the opposite side of the urethrovesical junction using a second support harness-vaginal shaft assembly and the same sling.

17. A method for the treatment of SUI, wherein the sling is placed submucosally, comprising the steps of, but not necessarily in the order of:
    (a) Placing patient in the lithotomy position;
    (b) Making a vertical suburethral incision along the vaginal mucosa of the anterior vaginal wall;
    (c) Dissecting submucosal connective tissue laterally, off of the vaginal wall;
    (d) Penetrating the anterior vaginal wall at a location approximately 2 cm lateral to the urethrovesical junction with the sharp leading end of a directional cannula delivery unit containing a support harness-vaginal shaft assembly;
    (e) Directing the cannula delivery unit in a cephalad direction along the posterior aspect of the pubic bone over the superior edge of the pubic bone;
    (f) Advancing the harness end of the assembly through the cannula delivery unit, down the anterior aspect of the pubic bone until the tip comes to rest at a position approximately halfway down the anterior aspect of the pubic bone;
    (g) Withdrawing the cannula delivery unit from the vagina exposing the tail of the vaginal shaft;
    (h) Coupling within the vaginal wall incision one end of the sling onto the vaginal shaft end of the assembly;
    (i) Adjusting the position of the sling submucosally within the vaginal wall incision until the appropriate position is achieved;
    (j) Securing the position of the sling and trimming excess vaginal shaft from the assembly;
    (k) Repeat steps d–j on the opposite side of the urethrovesical junction using a second support harness-vaginal shaft assembly and the same sling;
    (l) Closing vaginal mucosa incision.

18. A method for the treatment of SUI comprising the steps of, but not necessarily in the order of:
    (a) Placing patient in the lithotomy position;
    (b) Penetrating the abdominal wall at a location above the pubic symphysis and left of midline with the sharp leading end of a directional cannula delivery unit containing a support harness-vaginal shaft;
    (c) Directing the cannula delivery unit in a downward direction along the posterior aspect of the pubic bone penetrating the anterior vaginal wall and coming to rest just below the superior edge of the pubic bone;
    (d) Advancing the shaft end of the support harness-vaginal shaft assembly through the cannula delivery unit until the tip comes to rest in the vaginal cavity at a position approximately 2 cm lateral to the urethrovesical junction;
    (e) Directing the cannula delivery unit over the superior edge of the pubic bone;
    (f) Advancing the harness end of the support harness-vaginal shaft assembly up through the cannula delivery unit, down the anterior aspect of the pubic bone until the tip comes to rest halfway down the anterior aspect of the pubic bone;
    (g) Withdrawing the cannula delivery unit from the vagina exposing the tail of the vaginal shaft;
    (h) Coupling one end of the sling onto the vaginal shaft;
    (i) Adjusting the position of the sling against the anterior vaginal wall until the appropriate position is achieved;
    (j) Securing the position of the sling and trimming excess vaginal shaft from the assembly;
    (k) Repeat steps b–i on the opposite side of the urethrovesical junction using a second support harness-vaginal shaft assembly and the same sling;
    (l) Closing the abdominal wall cannula made incisions.

19. A method for the treatment of SUI, wherein the entry of the cannula delivery unit is through the abdominal wall and the sling is placed submucosally, comprising the steps of, but not necessarily in the order of:
    (a) Placing patient in the lithotomy position;
    (b) Making a vertical suburethral incision along the vaginal mucosa of the anterior vaginal wall;
    (c) Dissecting submucosal connective tissue laterally off of the vaginal wall;

(d) Penetrating the abdominal wall at a location above the pubic symphysis and left of midline with the sharp leading end of a directional cannula delivery unit containing a support harness-vaginal shaft;

(e) Directing the cannula delivery unit in a downward direction along the posterior aspect of the pubic bone penetrating the anterior vaginal wall and coming to rest just below the superior edge of the pubic bone;

(f) Advancing the shaft end of the support harness-vaginal shaft assembly through the cannula delivery unit until the tip comes to rest in the vaginal cavity at a position approximately 2 cm lateral to the urethrovesical junction;

(g) Directing the cannula delivery unit over the superior edge of the pubic bone;

(h) Advancing the harness end of the support harness-vaginal shaft assembly up through the cannula delivery unit, down the anterior aspect of the pubic bone until the tip comes to rest halfway down the anterior aspect of the pubic bone;

(i) Withdrawing the cannula delivery unit from the vagina exposing the tail of the vaginal shaft;

(j) Coupling within the vaginal wall incision one end of the sling onto the vaginal shaft;

(k) Adjusting the position of the sling submucosally within the vaginal wall incision until the appropriate position is achieved;

(l) Securing the position of the sling and trimming excess vaginal shaft from the assembly;

(m) Repeat steps d–l on the opposite side of the urethrovesical junction using a second support harness-vaginal shaft assembly and the same sling;

(n) Closing vaginal mucosa incision;

(o) Closing the abdominal wall cannula made incisions.

* * * * *